United States Patent [19]

Ioannou et al.

[11] Patent Number: 5,366,611
[45] Date of Patent: Nov. 22, 1994

[54] OXYGEN SENSOR

[75] Inventors: Andreas Ioannou; William C. Maskell, both of London, United Kingdom

[73] Assignee: British Gas plc, London, United Kingdom

[21] Appl. No.: 922,698
[22] Filed: Jul. 30, 1992

[30] Foreign Application Priority Data

Jul. 30, 1991 [GB] United Kingdom ............ 9116385.7

[51] Int. Cl.⁵ .......................................... G01N 27/417
[52] U.S. Cl. .................................... 204/412; 204/425; 204/426
[58] Field of Search .................... 204/153.18, 421–429, 204/412

[56] References Cited

U.S. PATENT DOCUMENTS

| | | | |
|---|---|---|---|
| 3,719,564 | 3/1973 | Lilly et al. | 204/426 |
| 3,843,400 | 10/1974 | Radford et al. | 204/421 |
| 4,025,412 | 5/1977 | Laconti | 204/426 |
| 4,207,159 | 6/1980 | Kimura et al. | 204/426 |
| 4,272,350 | 6/1981 | Croset et al. | 204/426 |
| 4,292,158 | 9/1981 | Muller et al. | 204/429 |
| 4,298,573 | 11/1981 | Fujishiro | 204/426 |
| 4,300,991 | 11/1981 | Chiba et al. | 204/426 |
| 4,304,652 | 12/1981 | Chiba et al. | 204/426 |
| 4,487,680 | 12/1984 | Logothetis et al. | 204/426 |
| 4,722,779 | 2/1988 | Yamada et al. | 204/426 |

Primary Examiner—T. Tung
Attorney, Agent, or Firm—Ware, Fressola, Van Der Sluys and Adolphson

[57] ABSTRACT

An oxygen sensor comprises a substrate 1 having two opposite faces, a first electrode layer 2 residing on one face of the substrate, an electrolyte 3 formed of a metal oxide oxygen ion conductor residing on the first electrode 2, a second electrode layer 4 residing on the electrolyte 3 wherein the electrodes 2 and 4 are formed of a material including a metal oxide oxygen ion conductor and a third electrode layer 6 residing on the other face of the substrate 1.

3 Claims, 3 Drawing Sheets

OXYGEN SENSOR

TECHNICAL FIELD

The present invention relates to an oxygen sensor.

BACKGROUND OF THE INVENTION

Oxygen sensors are used for inter alia the measurement and control of the air-to-fuel ratio in combustion systems such as automobile engines and gas-fired boilers. The sensor is situated in the exhaust gas and measurement of the oxygen content of the gas enables the efficiency of combustion and control of emissions to be optimised.

Typically an oxygen sensor comprises a substrate of alumina, a first electrode serving as a cathode residing on the substrate, a solid metal oxide oxygen ion conductor electrolyte residing on the cathode and a second electrode serving as an anode residing on the electrolyte. Typically the electrolyte is of zirconia while the electrodes are of platinum.

At present oxygen sensors of the type described comprise discrete electrode and electrolyte components. These sensors are relatively expensive however and to reduce the costs attempts have been made to fabricate the electrodes and the electrolyte as printed layers on the substrate. However, the sensors produced have suffered from a lack of adhesion between the platinum cathode and the electrolyte in particular and also between the platinum anode and the electrolyte as well and so printing of the sensors has not been a popular technique.

OBJECTS OF THE INVENTION

It is one object of the present invention to provide a sensor permitting diagnostic information pertaining to the correct functioning of the sensor to be obtained.

It is a further object of the invention to provide a sensor in which the adhesion between the cathode and the electrolyte is so improved that printing of the cathode and electrolyte layers may be undertaken with success.

It is a subsidiary object of the invention to provide a sensor in which the adhesion between the anode and the electrolyte is so improved that printing of the anode on the electrolyte may also be undertaken with success.

SUMMARY OF THE INVENTION

According therefore to one aspect of the present invention we provide an oxygen sensor comprising a substrate having two opposite faces, a first electrode layer residing on one face of the substrate, an electrolyte residing on the first electrode and a second electrode layer residing on the electrolyte and a third electrode layer residing on the other face of the substrate.

Preferably at least the first of the three electrodes is formed of a material including a metal-metal oxide oxygen ion conductor and the third electrode may also be formed of a material including a metal oxide oxygen ion conductor.

Conveniently the electrolyte is itself formed of a metal oxide oxygen ion conductor.

The substrate may be an oxygen ion conductor such as zirconia.

According to another aspect of the present invention we provide an oxygen sensor comprising a substrate having two opposite faces, a first electrode layer residing on one face of the substrate, an electrolyte formed of a metal oxide oxygen ion conductor residing on the first electrode and a second electrode layer residing on the electrolyte wherein at least the first of the two electrodes is formed of a material including a metal oxide oxygen ion conductor.

Preferably the second electrode is also formed of a material including a metal oxide oxygen ion conductor. The metal oxide may be zirconia and the substrate may be an oxygen ion conductor such as zirconia.

The metal oxide oxygen ion conductor in the electrode or electrodes may be the metal oxide part of a metal-metal oxide cermet and preferably the metal oxide of the electrode or electrodes and in the cermet is the same material which may be zirconia.

Suitably the metal in the cermet is platinum which conveniently comprises between 20% and 90% by volume of the cermet.

Embodiments of the invention will now be particularly described with reference to the drawings in which:

BEST MODE FOR CARRYING OUT THE INVENTION

Figure 1:
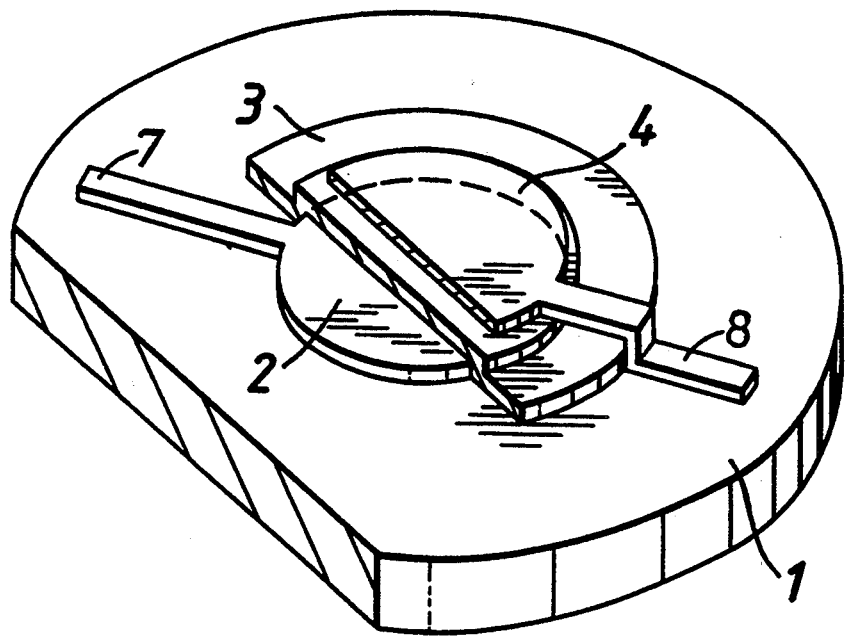
FIG. 1 shows a cutaway perspective view of one embodiment of the sensor.

Referring to FIG. 1, the sensor comprises a substrate 1, a first electrode 2 surmounting an upper face of the substrate 1, an electrolyte 3 surmounting the first electrode 2 and a second electrode 4 surmounting the electrolyte.

In the preparation of the sensor shown in FIG. 1, the substrate material selected was a 650 micron thick base of 96% alumina.

The ink material for both electrodes comprised a mixture of platinum paste and zirconia paste. The zirconia paste was made by mixing zirconia powder with commercial screen-printing binder and solvent. The platinum-zirconia cermet ink so formed comprised 12% by volume of platinum.

The electrolyte ink comprised the zirconia paste made by the process previously described.

The first electrode (to serve in use as the cathode) was then screen printed with a DEK, model 1202 machine onto the substrate 1 as the circular disc 2 with a radially extending tab 7 for connection to an electrical terminal as shown in FIG. 1. This was dried and briefly fired at 1000° C. to remove the organic binder prior to overprinting with the electrolyte.

Next, using the same machine, the electrolyte was screen printed over the cathode 2 also as a circular disc 3 overlapping the cathode 2 but leaving a part of the tab 7 to project beyond the periphery of the electrolyte 3. The electrolyte was dried and fired at 1400° C. for a period sufficient to sinter the zirconia.

Finally, the second electrode (to serve in use as the anode) was screen printed with the same machine over the electrolyte as a circular disc 4 of smaller diameter than that of the electrolyte 3 but also with a radially extending tab 8 for connection to an electrical terminal. The anode was then dried and briefly fired at 1400° C.

After firing the platinum content of the electrode was found to be 65% by volume.

The sensor was then cut as a disc of 8mm diameter from the substrate.

Finally platinum wires (not shown) to serve as electrical terminals were then connected to the anode and cathode.

The thickness of the electrode and electrolyte layers were controlled during printing, the resulting thickness of the electrode layers being 6 microns and of the electrolyte layer being 25 microns.

Figure 2:
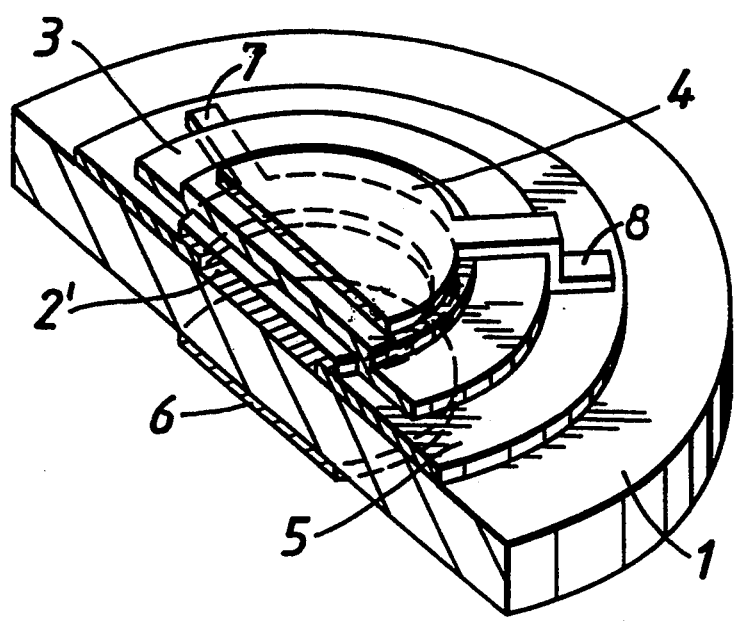
FIG. 2 shows a cutaway perspective view of another embodiment of the sensor.

Referring to FIG. 2 where identical components to the sensor shown in FIG. 1 bear identical reference numerals, this sensor also includes a non-electrically conducting layer 5 and a third electrode 6. In this case the substrate, 1, is an oxygen-ion conductor such as zirconia.

The layer 5 surmounts one face of the substrate 1 and has a central aperture through which extends a lower body of an electrode 2' similar in function to the electrode 2 of the first The lower body of the electrode 2' is in contact with sensor. The lower body of the electrode 2' is in contact with the upper face of the substrate 1 while the upper part of the electrode 2' has an annular projection 7 surmounting the layer 5. Surmounting the layer 5 is the electrolyte 3. The electrode 2' comprises a cermet of platinum and zirconia of similar nature and composition to the electrodes of the sensor in FIG. 1.

The third electrode 6 is disposed as shown on the underface of the substrate 1 and is provided with a radially extending tab (not shown) for connection to a platinum wire.

This electrode 6 also comprises a platinum-zirconia cermet of similar nature and composition to the electrodes of the sensor in FIG. 1.

The sensor shown in FIG. 2 is fabricated in a method similar to that described for the manufacture of the sensor of FIG. 1.

In the sensor of FIG. 1, in use, a voltage is applied between electrode 2 serving as the cathode and electrode 4 serving as the anode such that oxygen is reduced at the cathode and evolved at the anode, the current being carried by oxygen ions in electrolyte 3. This electrochemical process is known as oxygen pumping. The electrolyte 3 serves as a porous barrier restricting the transport of oxygen to the cathode 2. If a sufficient voltage is applied between the anode 4 and the cathode 2 the partial pressure of oxygen at the cathode 2 is reduced to a value close to zero. This is the limiting condition and the current flowing is controlled by the rate of diffusion of oxygen through the electrolyte 3. The limiting current is proportional to the oxygen concentration in the gas surrounding the sensor thereby rendering these sensors ideal for determining the oxygen concentration of exhaust gases in gas fired boilers and internal combustion engines to give but two examples of use.

In the sensor shown in FIG. 2, the voltage may additionally be measured between electrode 2' and electrode 6 while applying a voltage between electrode 2' serving as the cathode and electrode 4 (serving as an anode) to provide additional information from which oxygen concentrations may be measured and/or diagnostic information be obtained relating to the correct functioning of the sensor. For example, the third electrode may be used to ascertain that the sensor is operating in the linear region of its output current characteristic where the current is directly proportional to the partial pressure of the oxygen in the mixture. Operation in this region is highly desirable, since the response of the output current to changes in the temperature of the sensor is then a minimum. As a further example, a sensor incorporating a third electrode as described may be employed to perform functions such as those cited in UK Patent Application No. 9101763.2.

Figure 3:
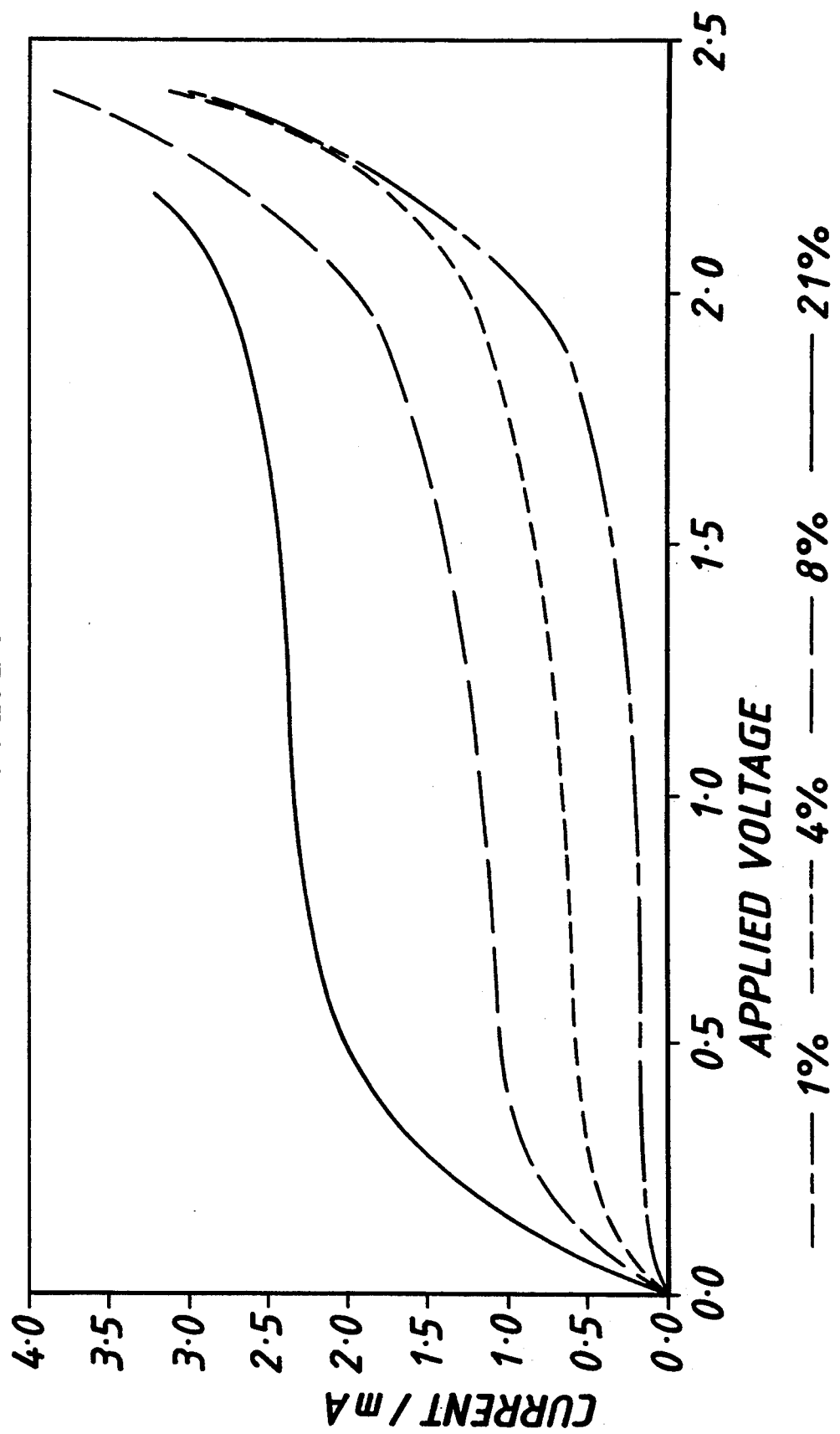
FIG. 3 shows the current-voltage characteristics of the first sensor embodiment at a constant temperature of 800° C. but with varying oxygen concentration
Figure 4:
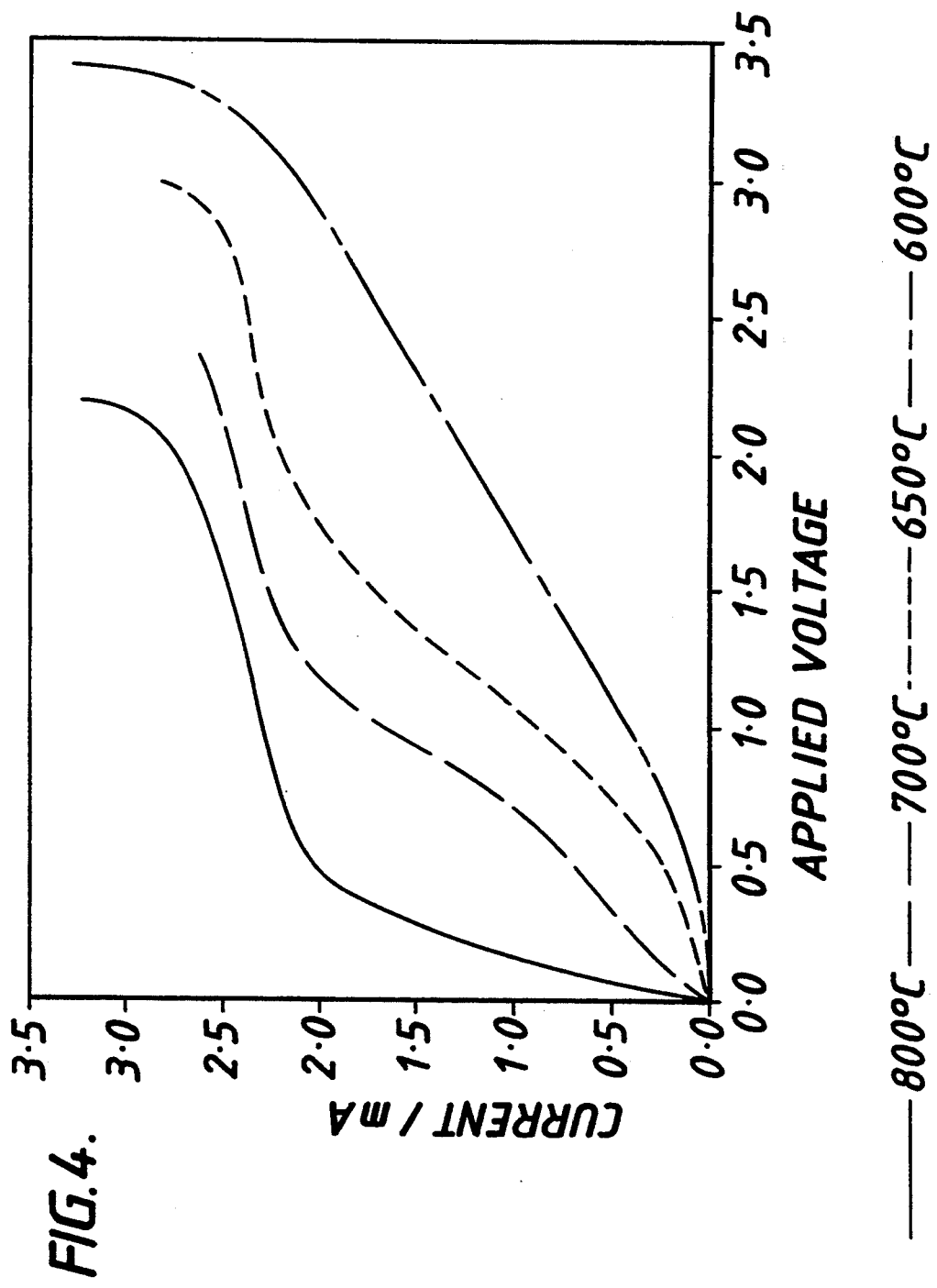
FIG. 4 shows the current-voltage characteristics of the first sensor embodiment at a constant oxygen concentration of 1% but varying temperature.

Referring to FIGS. 3 and 4, the sensor was located in a silica tube within a furnace, the temperature of which was variable. Oxygen concentration was controlled by mixing nitrogen and air together in defined ratios using mass flow valves. The gas mixture flowed through the silica tube and the current flowing through the sensor was measured for given voltages applied between the anode and cathode.

The current-voltage characteristics of the sensor at a fixed furnace temperature of 800° C. and oxygen concentrations of 1%, 4%, 8% and 21% by volume is shown in FIG. 3. These characteristics are very similar to those obtainable for sensors constructed from discrete components.

The current-voltage characteristics of the sensor at a fixed oxygen concentration of 21% by volume and furnace temperatures of 800° C., 700° C., 650° C. and 600° C. are shown in FIG. 4.

Again these characteristics are very similar to those obtainable for sensors constructed from discrete components.

The adhesion between the electrodes and the electrolyte was found to be excellent. It is believed that this is because both the electrolyte and each electrode contain an oxygen ion conductor specifically a metal oxide which in the case of this sensor is zirconia, thus rendering the electrolyte and electrodes physically compatible with each other for adhesion, particularly if the metal oxide in the electrolyte and in the electrodes is the same. Such improved adhesion properties are unobtainable when the electrode is a metal such as platinum, as is the case with conventional sensors.

We claim:

1. An oxygen sensor comprising:
   a substrate (1) having two opposite faces;
   a nonelectrically conducting layer (5) having a centrally arranged aperture and being arranged on one face of the substrate (1);
   a first electrode layer (2') being applied on a part of the nonelectrically conducting layer (5) and having a lower body portion extending through the centrally arranged aperture thereof and arranged on the one face of the substrate (1);
   an electrolyte layer (3) applied on and overlapping the first electrode layer (2');
   a second electrode layer (4) applied on the electrolyte (3);
   a third electrode layer (6) applied on the other face of the substrate (1),
   wherein the first electrode layer (2'), the electrolyte layer (3), the second electrode layer (4) and the third electrode layer (6) comprise a metal oxide oxygen ion conductor,
   whereby the first electrode layer (2'), the electrolyte layer (3), the second electrode layer (4) and the third electrode layer (6) are physically compatible with each other so the adhesion therebetween is excellent.

2. A sensor as claimed in claim 1 in which the substrate is an oxygen ion conductor.

3. A sensor as claimed in claim 2 in which the substrate is zirconia.

* * * * *

UNITED STATES PATENT AND TRADEMARK OFFICE
CERTIFICATE OF CORRECTION

PATENT NO. : 5,366,611
DATED      : November 22, 1994
INVENTOR(S): Ioannou et al.

It is certified that error appears in the above-indentified patent and that said Letters Patent is hereby corrected as shown below:

At column 3, line 25, please change "2'" to --2--.

Signed and Sealed this

Thirtieth Day of May, 1995

BRUCE LEHMAN

*Attest:*

*Attesting Officer*   *Commissioner of Patents and Trademarks*